United States Patent
Wruck et al.

(10) Patent No.: US 8,316,851 B2
(45) Date of Patent: Nov. 27, 2012

(54) ANESTHETIC GAS INTERMEDIATE STORAGE UNIT WITH ADSORPTION CHARACTERISTICS WHICH CAN BE INFLUENCED ELECTRICALLY

(75) Inventors: Norbert Wruck, Lübeck (DE); Michael Riecke, Lübeck (DE); Götz Kullik, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 1112 days.

(21) Appl. No.: 12/208,599

(22) Filed: Sep. 11, 2008

(65) Prior Publication Data

US 2009/0095296 A1 Apr. 16, 2009

(30) Foreign Application Priority Data

Oct. 11, 2007 (DE) .......................... 10 2007 048 892

(51) Int. Cl.
*A62B 7/10* (2006.01)
*A62B 18/00* (2006.01)

(52) U.S. Cl. .............................. 128/205.27; 128/200.24

(58) Field of Classification Search ............ 128/203.12–203.14, 203.17; 96/125, 111, 143, 146
See application file for complete search history.

(56) References Cited

U.S. PATENT DOCUMENTS

| 5,471,979 | A  * | 12/1995 | Psaros et al. ............ | 128/205.28 |
|---|---|---|---|---|
| 6,206,002 | B1  | 3/2001 | Lambert | |
| 6,488,028 | B1 * | 12/2002 | Lambert .................. | 128/205.12 |
| 7,077,134 | B2 * | 7/2006 | Ahlmen ................... | 128/205.12 |
| 2003/0075045 | A1 * | 4/2003 | Cowles et al. .................. | 95/148 |
| 2003/0199804 | A1 * | 10/2003 | Ahlmen et al. ............. | 604/6.09 |
| 2007/0079827 | A1 * | 4/2007 | Lambert .................. | 128/200.14 |
| 2007/0157929 | A1 * | 7/2007 | Radomski et al. ........ | 128/204.18 |
| 2009/0165800 | A1 * | 7/2009 | Broborg .................... | 128/205.12 |

FOREIGN PATENT DOCUMENTS

| EP | 1222940 A2 | 7/2002 |
|---|---|---|
| EP | 1440704 A1 | 7/2004 |
| FR | 2922113 A1 | 4/2009 |

* cited by examiner

*Primary Examiner* — Steven Douglas
*Assistant Examiner* — Rachel Young
(74) *Attorney, Agent, or Firm* — McGlew and Tuttle, P.C.

(57) ABSTRACT

An anesthetic gas intermediate storage unit is provided having a first gas duct for passing through inspiration gas, a second gas duct for passing through expiration gas and an adsorption material (2), which can be influenced electrically, for an anesthetic, which is carried by a gas. The adsorption material is arranged in at least one gas duct for passing through breathing gas, and with a device for admitting expiration gas and inspiration gas alternatingly to the adsorption material (2), at least at an identical area for the intermediate storage of the anesthetic from the expiration gas to the inspiration gas. The device has openings, which divert the expiration gas and inspiration gas flowing in and out such that expiration gas and inspiration gas are admitted to the stationary adsorption material (2) alternatingly at an identical area.

33 Claims, 8 Drawing Sheets

ANESTHETIC GAS INTERMEDIATE STORAGE UNIT WITH ADSORPTION CHARACTERISTICS WHICH CAN BE INFLUENCED ELECTRICALLY

CROSS REFERENCE TO RELATED APPLICATIONS

This application claims the benefit of priority under 35 U.S.C. §119 of German Patent Application DE 10 2007 048 892.2 filed Oct. 11, 2007, the entire contents of which are incorporated herein by reference.

FIELD OF THE INVENTION

The present invention pertains to an anesthetic gas intermediate storage unit (AGISU) and a process for respirating patients with intermediate storage of an anesthetic. The present invention pertains, furthermore, to an anesthetic gas module and a respiration system.

BACKGROUND OF THE INVENTION

Inhalation sedation of patients is used in intensive care units, especially following surgical procedures. Anesthetics, for example, sevoflurane or desflurane, are expensive substances, so that the consumption for the applications described shall be kept as low as possible. In addition, the release of anesthetics into the room air is to be kept within very low limits. Relatively simple anesthetic gas reflectors have hitherto been used sporadically, e.g., U.S. Pat. No. 6,206,002 B1, which transfer the anesthetic from the expiration gas expired by the patient to the inspiration gas to be inspired by the patient by means of uncontrolled adsorption and desorption of the anesthetic (so-called intermediate storage) and thus make it available for repeated use during breathing. The so-called intermediate storage efficiency is, however, compromised by various parameters. The following shall be mentioned here: high velocity of the breathing gas and very high (but physiologically desirable) moisture content in the breathing gas. The intermediate storage efficiency decreases, moreover, when the construction space of the absorber is reduced in order to save physiologically undesirable dead space.

However, the recycling of the anesthetic, which is attained under these conditions, lowers only the anesthetic consumption; a control or regulation, which would protect the patient and relieve the care staff, does not take place. However, there is a need in practice for adaptation to changed or special respiration situations (e.g., raising the concentration, application of high moisture levels in the breathing gas, high respiration rates). These can be attained by controlling the adsorption capacity.

SUMMARY OF THE INVENTION

The object of the present invention is to provide a respirator that makes possible the inhalation sedation of a patient that is suitable in a plurality of respiration situations by means of an electrically manipulated AGISU.

The object of the present invention is specifically to make available an AGISU, an anesthetic gas module and a respiration system as well as a process for the electrical manipulation of an AGISU during the artificial respiration of a patient, in which manipulation of adsorbent activated carbon fibers by means of directly influencing the temperature electrically is embodied.

The temperature dependence of adsorption processes is known from the area of technological principles. However, such a system must be able to be manufactured at a low cost and adequately from the viewpoint of the physiology of respiration for use in the field of medicine. The latter means that it must be guaranteed that the temperature can be influenced rapidly and in such a way that the influence is resolved for breaths, that the gas is heated only slightly, and that the dead space, which is relevant for rebreathing, is small.

This AGISU has an easy-to-regenerate adsorption material, which comes alternatingly into contact with expiration gas and inspiration gas and which again releases the anesthetic taken up during the expiration to the breathing gas during inspiration. A flexible tube connection means, which is moved preferably between two operating positions and alternatingly sends the gas to the adsorber beds filled with adsorption material and electrically connected adsorber beds, is present. The adsorption agent is firmly installed in the AGISU and is provided with electric contacts. The adsorption agent can be advantageously heated by applying electrical current with technically simple means and its adsorption properties can thus be influenced.

Same or identical flexible tube connection means are preferably arranged on both sides of the gas ducts for the purpose of feeding and removing the gas flows.

The avoiding of dead space, which is relevant for rebreathing, can be achieved in a favorable manner with a specific embodiment of the flexible tube connection means only, which will be described in detail below. In such an embodiment, the at least one means comprises a first gas line and a second gas line, designed such that the first and second gas lines are alternatingly movable between two operating positions relative to the adsorption agent, which can be electrically influenced. The first and second gas lines divert the expiration gas and the inspiration gas, which flows from the openings to the first and second gas ducts as well as from the first and second gas ducts to the openings. The gas lines connect the first and second gas ducts to the openings. The first and second gas lines are preferably designed as double lines each on both sides of the gas ducts.

A rotary motion can advantageously be carried out by the first and second gas lines.

In another embodiment, the at least one means comprises a drive means for moving the first and second gas ducts, e.g., at least one stationary electromagnet and at least one movable insertion magnet or an electric motor.

In an additional embodiment, the expiration gas and inspiration gas can flow through the adsorption material, which can be electrically influenced. An especially large adsorption surface is thus available. The adsorption material, which can be electrically influenced, preferably fills the two gas ducts completely, so that the inspiration gas and expiration gas flow through the entire adsorption material, which can be electrically influenced, and they have the smallest possible dead space.

In an additional embodiment, the first and second movable gas lines are designed as flexible tubes arranged concentrically one in the other, which are fixed at a distributor plate. The dead space can thus be reduced.

In another embodiment, a pipe fitting with a movable diaphragm forms the first and second gas lines, and the first and second gas lines are movable because of a motion, especially a rotary motion, of the diaphragm. The diaphragm divides the pipe fitting into the two gas lines preferably symmetrically.

In particular, the adsorption material, which can be influenced electrically, is designed as a cylindrical container, and a first part is separated in a gas-tight manner from a second part of the adsorption material, which can be influenced electrically, by a preferably symmetrically arranged partition.

In an additional embodiment, a first part and a second part of the adsorption agent, which can be influenced electrically, are arranged in a carrier unit in two preferably duct-shaped recesses as gas lines of the carrier unit.

The carrier unit preferably has a third and fourth, preferably duct-shaped recess for flooding the AGISU with fresh breathing gas and/or for an oxygen flush. The at least one means may preferably also assume a third operating position for this.

The adsorption agent, which can be influenced electrically, preferably consists at least partly of carbon fibers.

In an advantageous embodiment, the adsorption agent, which can be influenced electrically, can be heated, for example, by electric current being able to be sent through the material by means of electrodes or by electric heating wires being integrated in the material.

In an additional embodiment, the first and second parts of the adsorption agent, which can be influenced electrically, can be heated separately. This heating is used to accelerate the desorption or also to sterilize the adsorption unit.

In another embodiment, the adsorption material, which can be influenced electrically, or the adsorption material, which can be influenced electrically, including the container or the carrier unit, can be removed from the AGISU. The adsorption agent, which can be influenced electrically, can thus be sterilized in a simple manner. However, it is also possible to heat the adsorption material directly and to sterilize it directly without removal.

The AGISU advantageously comprises a housing. The first and second gas ducts with the adsorption agent, which can be influenced electrically, and preferably also the means for diverting the expiration gas and the inspiration gas, are arranged in the housing.

In another embodiment, the at least one means comprises at least one air valve and/or at least one valve, which can be moved preferably by a drive means, e.g., a magnet. Instead of the movable gas lines, it is also possible to use air valves or valves, preferably in connection with stationary gas lines, for diverting the expiration gas and inspiration gas flowing in and out through the openings. It is also possible to combine the movable gas lines for diverting and the air valves or valves for diverting with one another, i.e., the movable gas lines are arranged on one side of the gas ducts and the air valves or valves are arranged on the other side of the gas ducts.

An anesthetic gas module according to the present invention with an AGISU comprises a set point adjuster, ports for connecting a respirator and a flexible expiration tube and a flexible inspiration tube for respirating the patient, preferably drive means, preferably a control unit with a regulator, preferably an anesthetic dispenser, preferably an adsorption filter, preferably a breathing phase detector, preferably an anesthetic measuring device, preferably signal and data lines to connect the anesthetic measuring device and/or the anesthetic dispenser and/or the breathing phase detector and/or the drive means to the control unit, and preferably an electrical contact for connecting the control unit to a respirator by means of a signal line.

A respiration system according to the present invention with a respirator, with an AGISU and with a flexible expiration tube and with a flexible inspiration tube for respirating a patient comprises an above-described AGISU or an above-described anesthetic gas module.

In a process according to the present invention for the intermediate storage of an anesthetic during the artificial respiration of a patient, the expiration gas and inspiration gas are alternatingly admitted at least at one identical area to a stationary adsorption material, which can be influenced electrically and which is arranged in a gas duct or in both gas ducts, for an anesthetic carried by a gas, for the intermediate storage of the anesthetic from the expiration gas to the inspiration gas, wherein the expiration gas and inspiration gas flowing in and out through the openings is alternatingly diverted, so that inspiration gas and expiration gas flow alternatingly through the first gas duct and expiration gas and inspiration gas flow alternatingly through the second gas duct, and the inspiration gas and expiration gas are alternatingly admitted as a result to the adsorption material, which can be influenced electrically, at the at least one identical area.

In another embodiment, a first gas line and a second gas line are moved alternatingly between two operating positions relative to the adsorption agent, which can be influenced electrically, in order to divert the expiration gas and inspiration gas flowing in and out.

The first and second gas lines advantageously perform a rotary motion.

The first and second gas lines are moved between the two operating positions after one to three breathing cycles in another embodiment.

The expiration gas and inspiration gas, which flow through the first and second gas ducts, are preferably admitted alternatingly to a first part and a second part of the adsorption material, which can be influenced electrically.

In an additional embodiment, the inspiration gas and expiration gas are preferably sent completely through the adsorption material, which can be influenced electrically.

The adsorption material, which can be influenced electrically, is advantageously heated.

In another embodiment, the adsorption material, which can be influenced electrically, and to which inspiration gas is admitted, is heated during and/or shortly before the admission of inspiration gas in order to increase the concentration of the anesthetic in the inspiration gas.

In an additional embodiment, the adsorption material, which can be influenced electrically and to which expiration gas is admitted, is heated during and/or shortly before the admission of expiration gas in order to lower the concentration of the anesthetic in the inspiration gas of a subsequent breathing cycle.

The adsorption material, which can be influenced electrically, is preferably heated for sterilization.

In another embodiment, electric current is sent through the adsorption material, which can be influenced electrically, to sterilize the adsorption material, which can be influenced electrically.

The electric current is preferably sent through different segments of the adsorption material, which can be influenced electrically.

In an additional embodiment, the electric current is sent with different voltages through the adsorption material, which can be influenced electrically.

In an additional embodiment, at least one air valve and/or at least one valve is moved preferably by a drive means, e.g., a magnet, for diverting the expiration gas and inspiration gas flowing in and out through the openings.

The present invention comprises, furthermore, a computer program with program code means, which are stored on a computer-readable data storage medium, in order to carry out an above-described process when the computer program is run on a computer or on a corresponding computing unit.

In addition, a computer program product with program code means, which are stored on a computer-readable data storage medium, in order to carry out an above-described process when the computer program is run on a computer or on a corresponding computing unit, is part of the present invention.

An exemplary embodiment of the present invention will be described in greater detail below with reference to the drawings attached. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
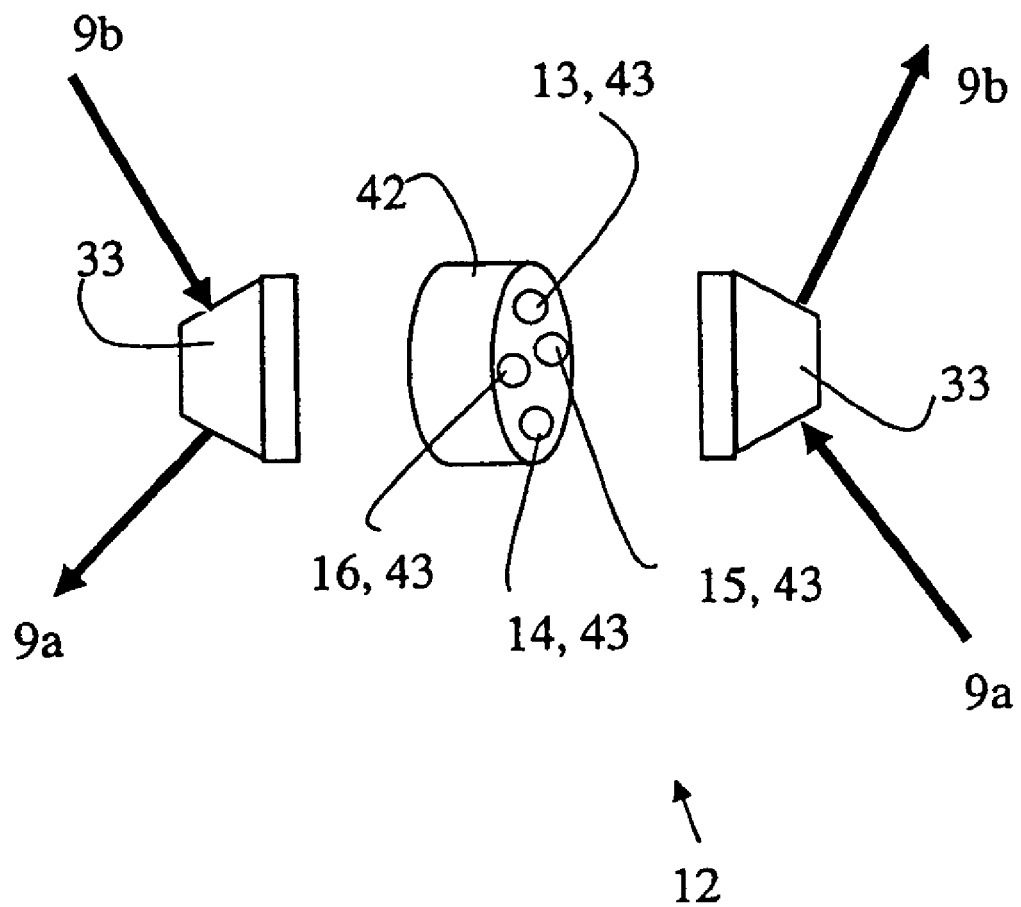
FIG. 1 is a schematic perspective view of an anesthetic gas intermediate storage unit according to the present invention.
Figure 2:
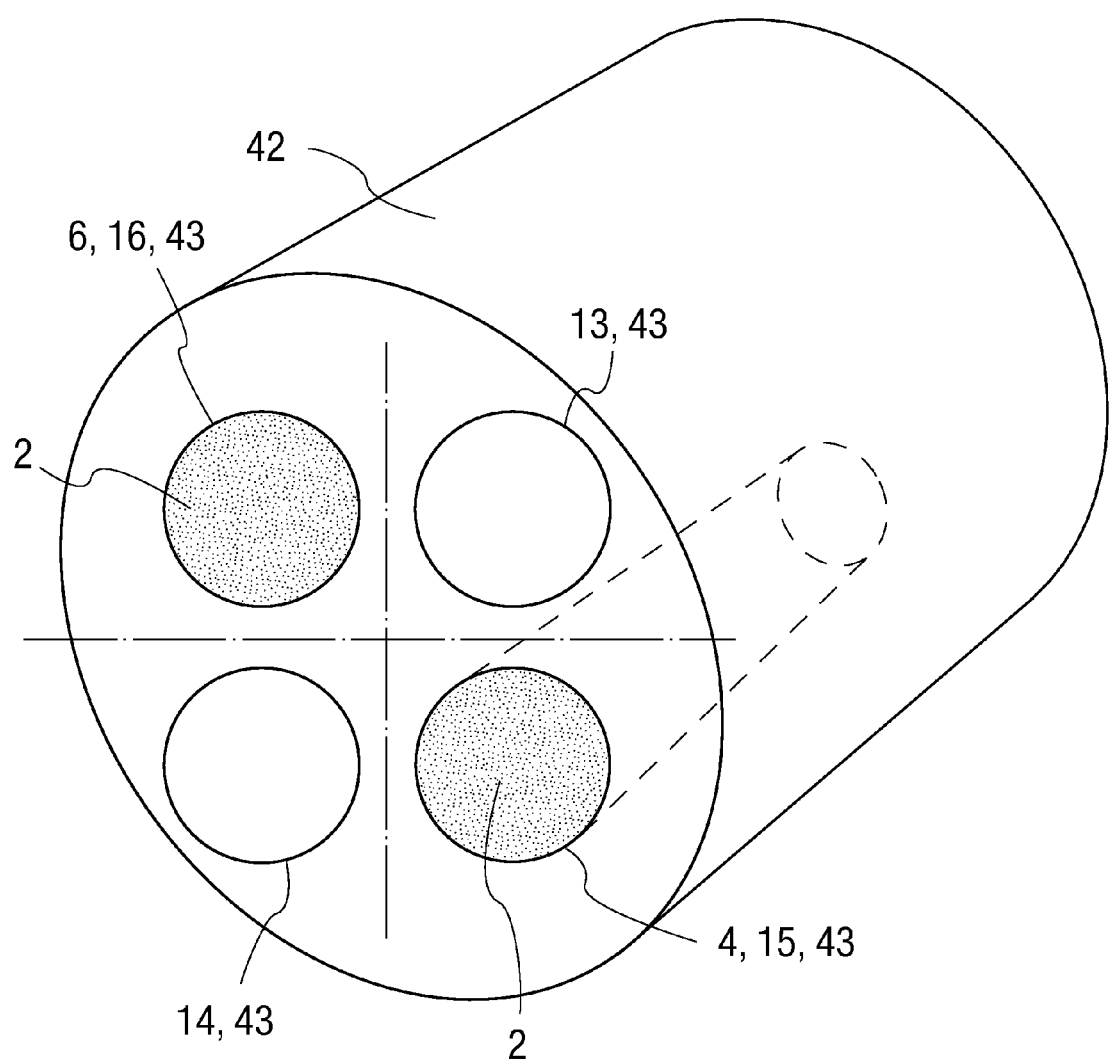
FIG. 2 is a perspective view of a carrier unit.

Referring to the drawings in particular, FIG. 1 shows a perspective view of an anesthetic gas intermediate storage unit 12 according to the present invention for the intermediate storage of anesthetic during the artificial respiration of a patient. The anesthetic gas intermediate storage unit 12 comprises a first gas line 9a on a first side for passing through expiration air and a second gas line 9b for passing through inspiration air. Both gas lines 9a, 9b are connected to a movable pivoting means 33, so that the gas lines 9a, 9b are movable. The two gas lines 9a, 9b are also formed on a second side (FIG. 1, right) of a carrier unit 42 analogously to the first side of the carrier unit 42. The carrier unit 42 may be cylindrical and stationary (FIGS. 1 and 2), for example, and made of a heat-resistant plastic or metal, and provided with four cylindrical recesses 43, which pass completely through the carrier unit 42 (only one recess 43 is shown completely by dash-dotted line in FIG. 2). Two recesses 43 are used as adsorber beds 15, 16, i.e., they form a first stationary gas duct and a second stationary gas duct 4, 6, respectively, and are filled completely with two separate parts 15, 16 of an adsorption material 2, which can be influenced electrically, and which has a diameter of 40 mm to 50 mm (FIG. 2) for a volatile anesthetic carried by a gas, e.g., for halothane, enflurane, sevoflurane, isoflurane, or desflurane. The other two recesses 43 act as empty beds 13, 14. Pivoting of the two gas lines 9a, 9b on the two sides of the carrier unit 42 makes it possible to send expiration gas through the adsorber bed 15 as a first gas duct and inspiration gas through the adsorber bed 16 as a second gas duct 6 in a first operating position A. The adsorption material 2, which can be influenced electrically and is present in the adsorber bed 15, adsorbs, for example, 90% of the anesthetic present in the expiration gas and is thus enriched with anesthetic. Furthermore, the adsorption material 2, which can be influenced electrically and is arranged in the adsorber bed 16, desorbs anesthetic into the inspiration gas. For the intermediate storage of the anesthetic, the two gas ducts 4, 6 are moved by means of the pivoting means 33 after about one to three breathing cycles, so that expiration gas flows through the adsorber bed 16 and inspiration gas through the adsorber bed 15 in a second operating position C. The adsorption material 2, which can be influenced electrically and is present in the adsorber bed 16, is thus enriched with anesthetic. The gas lines 9a, 9b assume their first operating position A again after another one to three breathing cycles. The fact that the gas lines 9a, 9b repeatedly assume the first and second operating positions A, C makes possible the intermediate storage of the anesthetic during a longer artificial respiration operation. In a third operating position B of the gas lines 9a, 9b, the expiration gas and inspiration gas are sent through the recesses 43, which are designed as empty beds 13, 14 and which contain no adsorption material 2, which can be influenced electrically. The anesthetic gas intermediate storage unit 12 can thus be ventilated with fresh gas or fresh air, i.e., intermediate storage of the anesthetic can be prevented.

Figure 3:
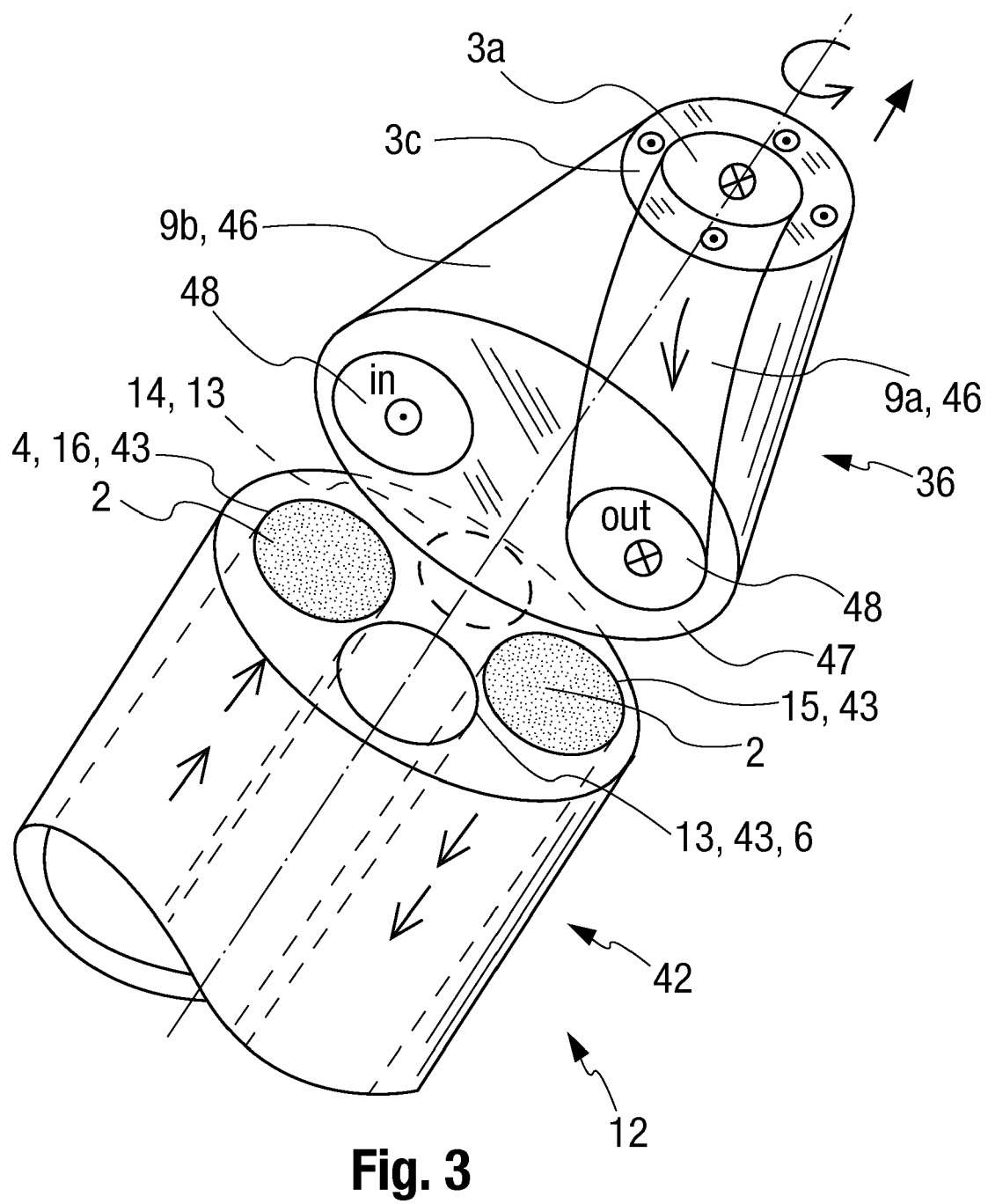
FIG. 3 is a perspective partially sectional view of the carrier unit with a rotatable distributor fitting.
Figure 4:
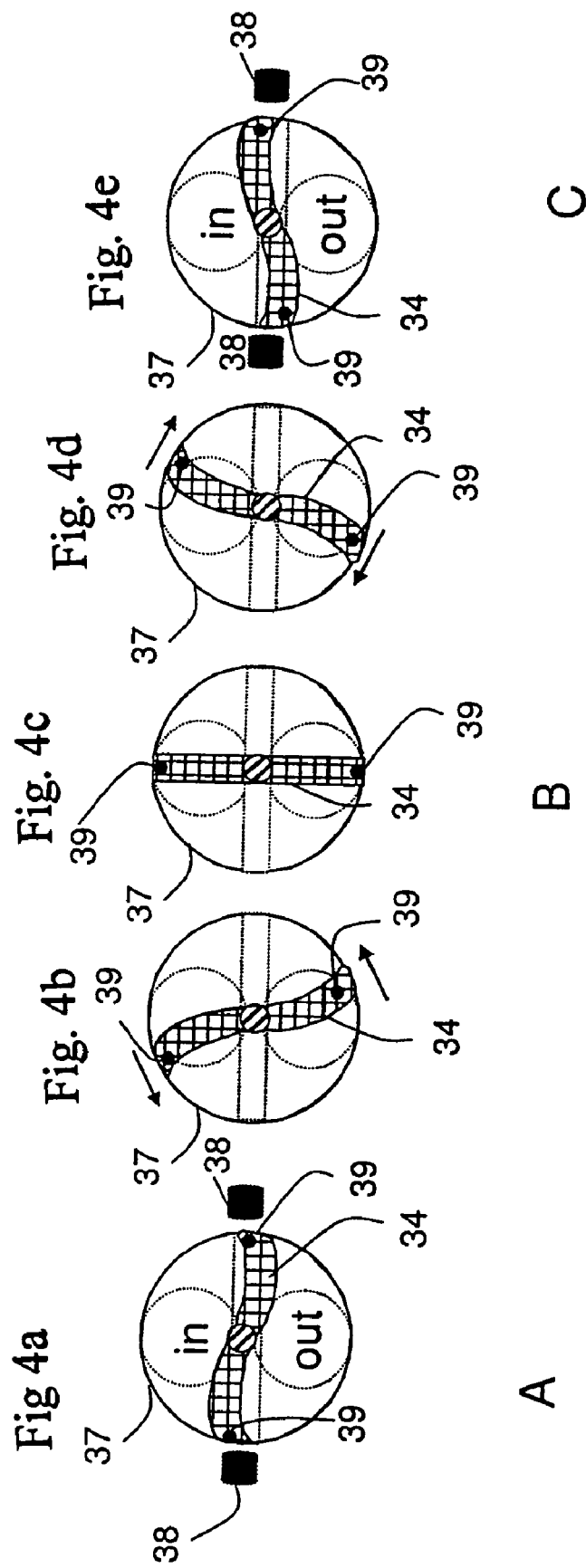
FIG. 4a is a cross sectional view of a flexible tube formed by a pipe fitting and a movable diaphragm in one of different operating positions.
FIG. 4b is a cross sectional view of a flexible tube formed by a pipe fitting and a movable diaphragm in another of different operating positions.
FIG. 4c is a cross sectional view of a flexible tube formed by a pipe fitting and a movable diaphragm in another of different operating positions.
FIG. 4d is a cross sectional view of a flexible tube formed by a pipe fitting and a movable diaphragm in another of different operating positions.
FIG. 4e is a cross sectional view of a flexible tube formed by a pipe fitting and a movable diaphragm in another of different operating positions.

FIG. 3 shows the anesthetic gas intermediate storage unit 12 with the carrier unit 42 and with a distributor fitting 36. The distributor fitting 36 has a distributor plate 47 with two holes 48. A first gas line 9a, designed as a flexible tube 46, for passing through expiration gas, and a second gas line 9b, likewise designed as a flexible tube 46, for passing through inspiration gas, are arranged at the distributor plate 47. The two gas lines 9a, 9b are arranged concentrically one in the other, and each gas line 9a, 9b opens into a hole 48 each of the distributor plate 47 and the flexible tube 46 flares up conically towards the flexible tube 46 for guiding inspiration air. Thus, the distributor fitting 36 forms a port, which is nearly free from dead space. The two ends of the gas lines 9a, 9b form a first opening 3a for introducing expiration gas and a second opening 3c for discharging expiration gas. A second distributor fitting 36 on the underside with the openings 3b and 3c is not shown. Twisting of the distributor plate 47 thus makes it possible, according to the principle described above in connection with FIG. 1, to reflect the anesthetic from the expiration gas to the inspiration gas or to flood the anesthetic gas intermediate storage unit 12 with fresh gas.

Figure 5:
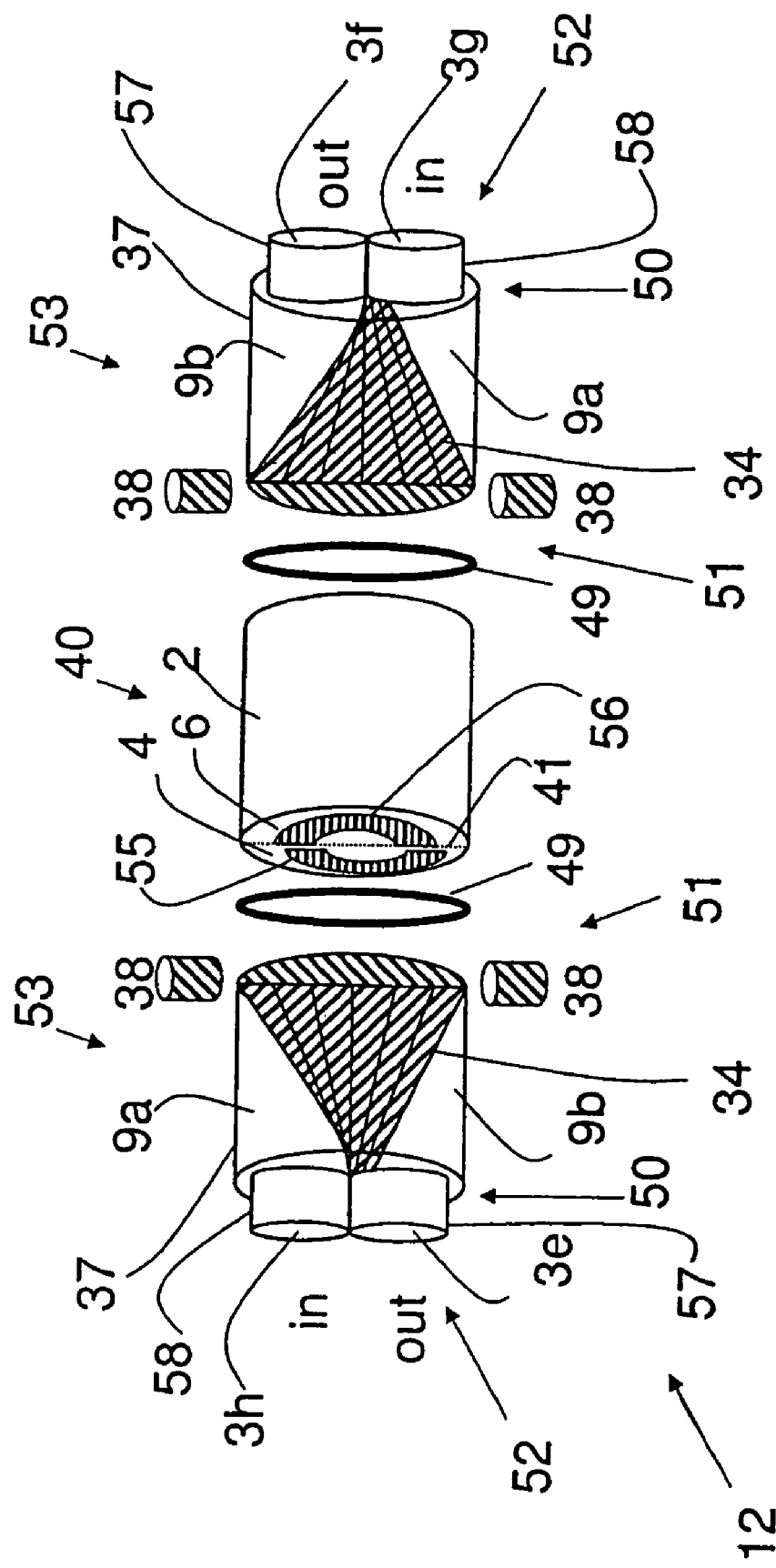
FIG. 5 is an exploded perspective view of an adsorption material for an anesthetic carried by a gas, which adsorption material is designed as a cylindrical container (center) and which can be influenced electrically, with two flexible tubes on the respective two sides of the container.

FIGS. 4a, 4b, 4c, 4d, 4e and 5 show another embodiment of the movable first and second gas lines 9a, 9b. A pipe fitting 37 is divided symmetrically in the longitudinal direction by a movable diaphragm 34 into first and second gas lines 9a, 9b, so that a flexible tube 53 is present. Pipe fitting 37 is provided at a first end 50 with a double port socket 52, comprising a port socket 57 for expiration gas and a port socket 58 for inspiration gas, for connecting a flexible expiration tube and a flexible inspiration tube 59, 60, respectively. Port socket 57 thus forms a first opening 3e for admitting inspiration gas and port socket 58 forms a fourth opening 3h for releasing inspiration gas. A second opening 3f for releasing expiration gas and a third opening 3g for admitting inspiration gas are analogously formed on the other flexible tube 53 (FIG. 5, right). At the second end 51, the pipe fitting 37 is connected by means of a sliding sealing ring 49 to the adsorption material 2, which can be influenced electrically, and which is designed as a cylindrical container 40. The cylindrical container 40 is provided with a partition 41 extending symmetrically in the longitudinal direction, so that the absorption material 2, which can be influenced electrically, is divided into two separate parts 55, 56. The two separate parts of the adsorption material 2, which can be influenced electrically, thus form two gas ducts 4, 6. A pipe fitting 37 each is arranged at the two ends of the container 40 (FIG. 5, left and right). The movable diaphragm 34 is a stationary diaphragm at the first end 50 of pipe fitting 37 and diaphragm 34 can perform a rotary motion by 180° at the second end 51 of the pipe fitting 37. FIGS. 4a-4e show in a cross section at the second end 51 of pipe fitting the operating positions A, B and C as well as in the intermediate positions of diaphragm 34 during the rotary motion of diaphragm 34 from operating position A into operating position B and from operating position B to operating position C. Diaphragm 34 performs a rotary motion by 180° at the second end 51 of pipe fitting 37 (cross section according to FIGS. 4a-4e) and is stationary at the first end 50 of pipe fitting 37. Diaphragm 34 performs a correspondingly smaller rotary motion in the positions located in between in the longitudinal direction of pipe fitting 37. To return the flexible tube 53 from operating position C into operating position A, diaphragm 34 is again turned back by 180° in the opposite direction compared to what is shown in FIGS. 4a-4e, so that a nearly dead space-free connection is possible. The rotary motion of diaphragm 34 is performed by means of two electromagnets 38 and two insertion magnets 39. The electromagnets 38 may assume different magnetic polarities, so that diaphragm 34 is moved by 180° when the polarities are switched over. The expiration gas and inspiration gas can thus be admitted to the two separate parts 55, 56 of the adsorption material 2, which can be influenced electrically, alternatingly at identical areas, i.e., the parts 55, 56, so that the anesthetic is reflected by the expiration gas to the inspiration gas. Operating position B is the zero position or short-circuit position.

Figure 6:
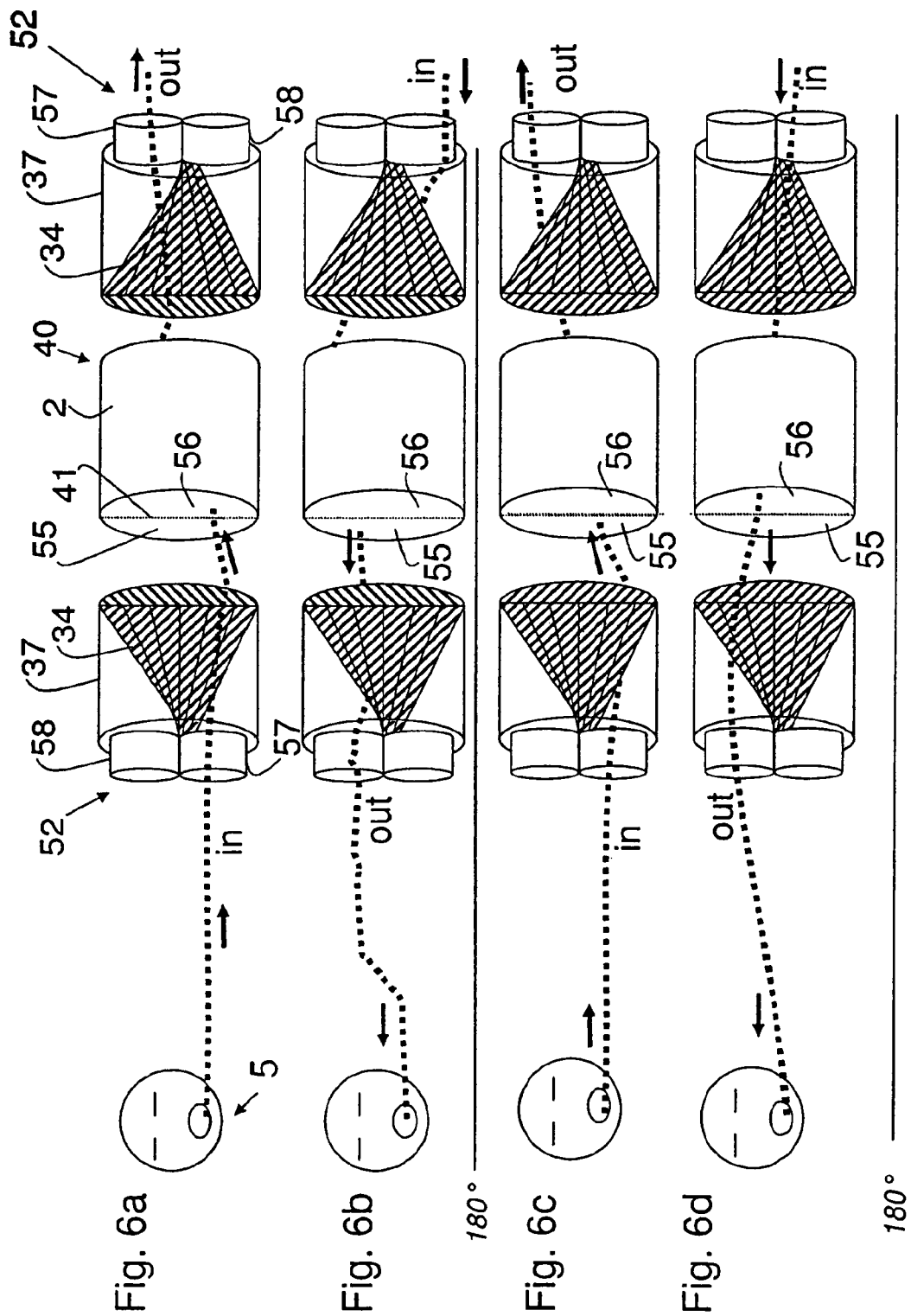
FIG. 6a is a perspective view of the container with the two flexible tubes according to FIG. 5 in an operating position A and the path of the expiration gas.
FIG. 6b is a perspective view of the container with the two flexible tubes according to FIG. 5 in an operating position A and the path of the inspiration gas.
FIG. 6c is the perspective view of the container with the two flexible tubes according to FIG. 5 in an operating position C and the path of the expiration gas.
FIG. 6d is a perspective view of the container with the two flexible tubes according to FIG. 5 in an operating position C and the path of the inspiration gas.

The path of flow of the expiration gas and inspiration gas through parts 55, 56 of the adsorption material 2, which can be influenced electrically, is shown in FIGS. 6a through 6d in the two operating positions A and C of the flexible tubes 53 with a port socket 57 for expiration gas and a port socket 58 for inspiration gas. During expiration by the patient 5, the expiration gas is flowing through part 56 of the adsorption material 2, which can be influenced electrically, in operating position A (FIG. 6a), so that part 56 is adsorbing anesthetic. During the subsequent inspiration in operating position A, the inspiration gas is flowing through part 55 of the adsorption material 2, which can be influenced electrically (FIG. 6b). The inspiration gas is enriched by the anesthetic desorbed at part 55. The diaphragm is rotated by 180° for the operating position C shown in FIGS. 6c and 6d. The expiration gas is flowing in operating position C through part 55 and the inspiration gas is flowing through part 56, i.e., opposite to what happens in operating position A. Part 56 can thus desorb the anesthetic adsorbed in operating position A into the inspiration gas, i.e., the anesthetic is reflected. Furthermore, part 55 adsorbs anesthetic and desorbs it again in a subsequent operating position A to the inspiration gas. The operating positions A and C are mutually changed, in general, after one to three breathing cycles of patient 5.

For example, carbon fibers or carbon mats with a large specific area of approximately 2,000 $m^2$ per g are used, for example, as adsorption material 2, which can be influenced electrically. An active adsorption area of approximately 2,000 to 5,000 $m^2$ is needed for an anesthesia reflector 12 according to the present invention, i.e., the adsorption material 2, which can be influenced electrically, has a low weight of a few g. The layer thickness of parts 55, 56, i.e., the length of the flow path in the adsorption material 2, which can be influenced electrically, should be selected so as to ensure that the pressure drop does not exceed 0.5 mbar at 60 L of breathing gas per minute.

The adsorption material 2, which can be influenced electrically, can be heated by passing through electric current. The concentration of the anesthetic can thus be controlled. The heating of a part 55, 56 of the adsorption material 2, which can be influenced electrically, through which said part the inspiration gas flows, during the flowthrough of inspiration gas increases the desorption of the anesthetic, so that the concentration of the anesthetic in the inspiration gas can be increased thereby, especially during the initial phase. Conversely, the heating of the part 55, 56 of the adsorption material 2, which can be influenced electrically, through which said part expiration gas flows, during the flowthrough of expiration causes the corresponding part 55, 56 to adsorb less anesthetic or it even causes anesthetic to be desorbed, so that less anesthetic will be released to the inspiration gas during a subsequent inspiration in another operating position, because the part 55, 56 in question has adsorbed less anesthetic. Because of the lower mass of the anesthetic, which can be influenced electrically, the heating and cooling can be carried out in a very short time, so that the heated part 55, 56 will already have been cooled completely or nearly completely in a next operating position.

Furthermore, sterilization and disinfection can be carried out at sufficiently high temperatures in the range of 100° C. to 180° C., outside the operation of the adsorption material 2, which can be influenced electrically, due to the heating of the two parts 55, 56, i.e., of the entire adsorption material 2, which can be influenced electrically. Thus, it is not necessary to remove the adsorption material 2, which can be influenced electrically, for this purpose.

Figure 7:
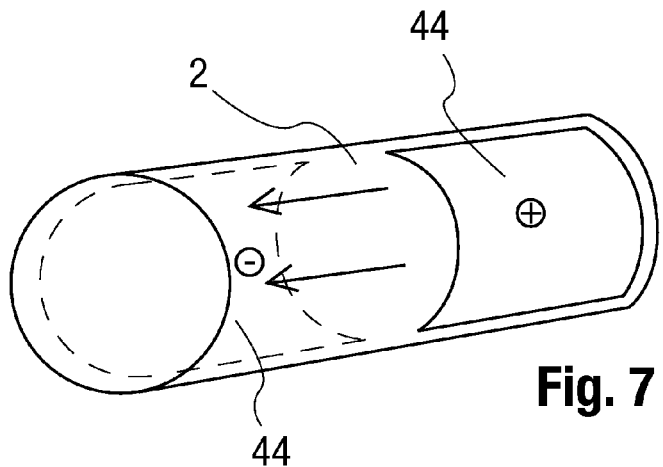
FIG. 7 is a first embodiment of adsorption material, which adsorption material can be influenced electrically, for an anesthetic carried by a gas, with two electrodes for being introduced into a recess of the carrier unit.

FIG. 7 shows the arrangement of two electrodes 44 on the surface of a cylindrical adsorption material 2, which can be influenced electrically, for being introduced into the recess 43 or the adsorber bed 15, 16 of the carrier unit 42. The electric current flows in the adsorption material 2, which can be influenced electrically, from the positive electrode 44 according to the arrow to the negative electrode 44.

Figure 8:
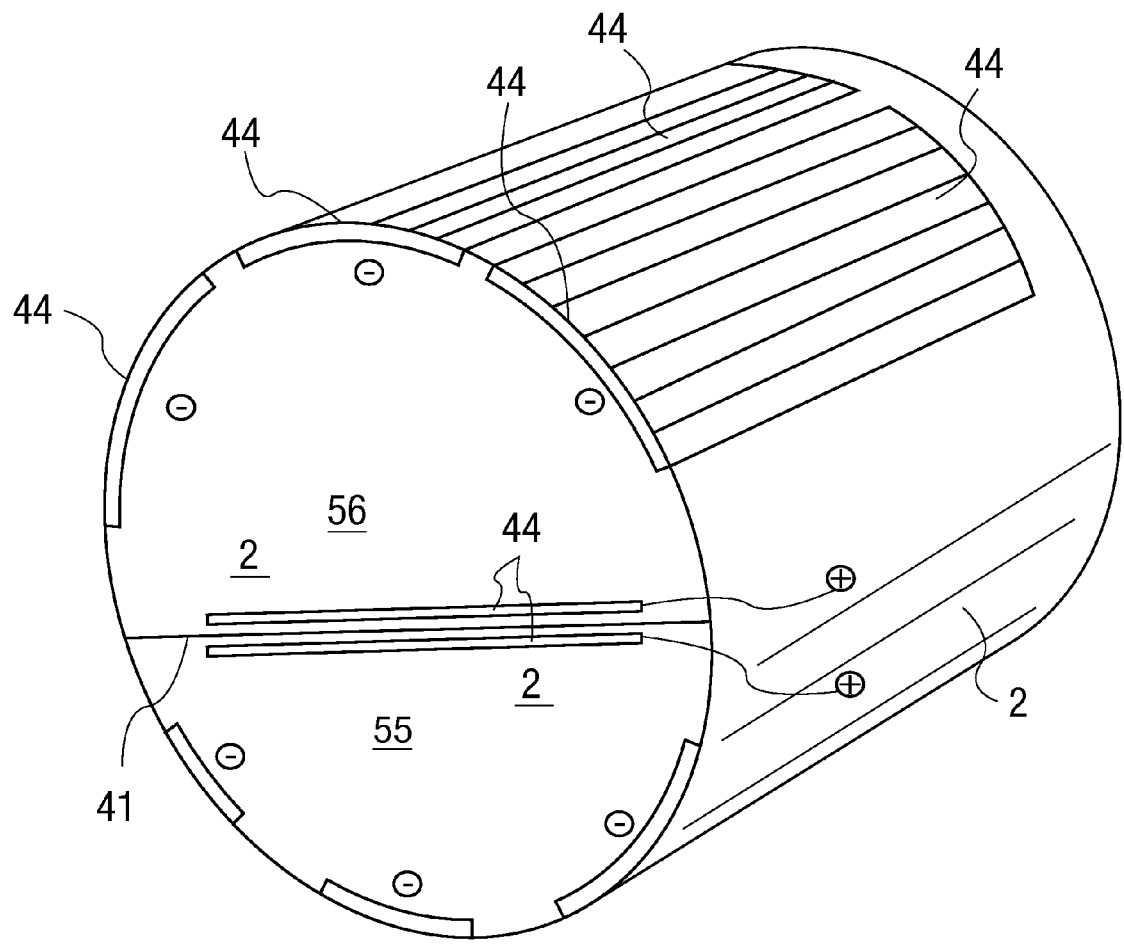
FIG. 8 is a second embodiment of the adsorption material, which adsorption material can be influenced electrically, for an anesthetic carried by a gas, with a plurality of electrodes, as a cylindrical container.

FIG. 8 shows the design of the electrodes 44 for the adsorption material 2, which can be influenced electrically and is designed as a cylindrical container. Three negatively charged electrodes 44 are arranged on the outside for each part 55, 56, and a positively charged electrode 44 is arranged each on both sides of the partition 41. A negative charge is intermittently sent to the three negative electrodes 44, i.e., the electric current flows rotatingly between the positively charged electrode 44 and the alternatingly negatively charged electrodes 44. Furthermore, a homogeneous temperature distribution can also be attained in the parts 55, 56 by using different voltages while simultaneously applying current to the three negative electrodes 44.

The adsorption material 2, which can be influenced electrically, and/or the adsorber beds 15, 16 are preferably equipped with temperature sensors (not shown). The electrodes 44 can be attached to the adsorption material 2, which can be influenced electrically, by means of a conductive adhesive, by clamping or by tamping. Rough or toothed electrodes may be used to enlarge the contact area between the electrodes 44 and the adsorption material 2, which can be influenced electrically. The surface or the edges of the adsorption material 2, which can be influenced electrically, may be partially provided with a metal coating in order to improve the contact and/or to enlarge the contact area.

Instead of an adsorption material 2 of a round shape, which can be influenced electrically, it is also possible to select a shape with a polygonal cross section or with a cross section having n corners. The electrodes 44 are now arranged at the flat outer surfaces between the corners opposite each other and current is admitted to them intermittently at electrodes 44 that are preferably located opposite each other. A shape with corners in the cross section has the advantage of being able to be better contacted electrically, but it may not be possible to guarantee uniform flowthrough of gas with this shape having n corners.

The electric power needed to heat up parts 55, 56 is approximately 10 W to 50 W during an expiration or inspiration phase. A voltage below 60 V d.c. or below 25 V in case of alternating current is selected for safety reasons.

Figure 9:
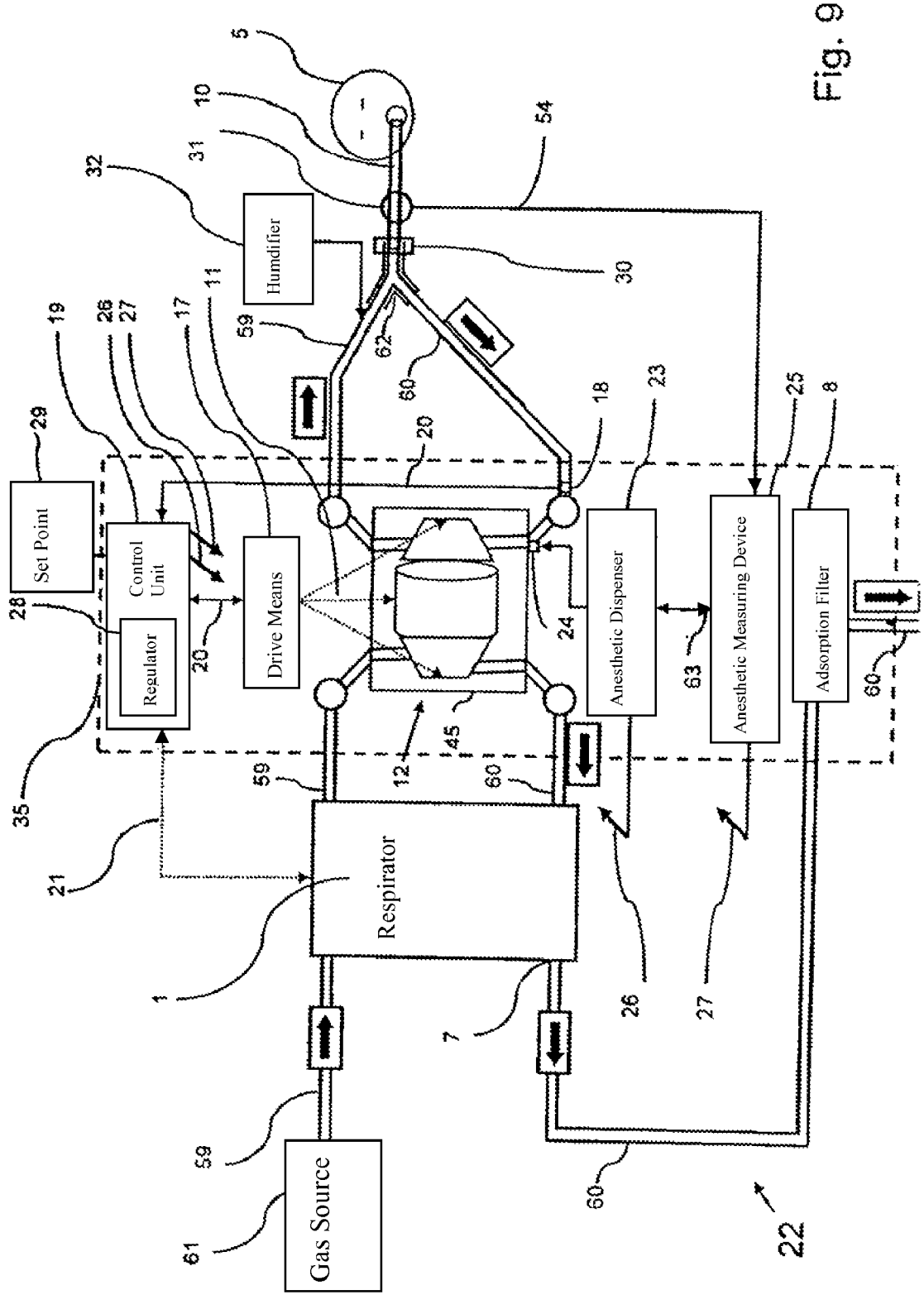
FIG. 9 is a schematic view of a respiration system according to the present invention with the anesthetic gas intermediate storage unit according to the present invention.

FIG. 9 shows a respiration system 22 according to the present invention with an anesthetic gas intermediate storage unit 12 according to the present invention. An anesthetic gas module 35 according to the present invention comprises, besides the anesthetic gas intermediate storage unit 12, a set point adjuster 29 for controlling the concentration of anesthetic in the inspiration gas with the control unit 19 and with the regulator 28 for the anesthetic concentration. For example, the concentration can be set to values between 0.5 vol. % and 4.0% and especially 1.0% as a function of the anesthetic in the inspiration gas. A connector 11 connects an electric drive means 17 to the anesthetic gas intermediate storage unit 12. The signal line 21 is used to synchronize the respirator 1, e.g., with a fan (not shown), with the anesthetic gas intermediate storage unit 12 and for data exchange. The respirator 1 is supplied with fresh gas, e.g., oxygen, from a pressurized gas source 61. The inspiration gas then flows through the flexible inspiration tube 59 to the anesthetic gas intermediate storage unit 12 with the housing 45, it is enriched with anesthetic there and flows through a Y-piece 62 by means of the breathing tube 10 to the patient 5. An HME filter 30 is arranged in the breathing tube 10 as a heat and moisture exchanger and an anesthetic gas tapping point 31. In addition, a humidifier 32, which feeds moisture into the inspiration gas if an HME filter 30 cannot be used, is located at the flexible inspiration tube 59 at a short distance in front of the Y-piece 62. The anesthetic gas tapping point 31 takes inspiration gas or expiration gas at the breathing tube 10 for determining the actual value of the anesthetic concentration and sends these through a measuring line 54 to the anesthetic measuring device 25. For example, 50 mL/minute to 200 mL/minute are sent through the measuring line 54. The anesthetic dispenser 23 and the anesthetic measuring device 25 are connected to the control unit 19 by means of signal lines 26, 27. To add anesthetic with the anesthetic dispenser 23, the inspiration gas or expiration gas taken at the anesthetic gas tapping point 31 is enriched with anesthetic by the anesthetic dispenser 23 and fed through the anesthetic port 24 to the flexible expiration tube 60 at a short distance in front of the anesthetic gas intermediate storage unit 12. The inspiration gas or expiration gas taken is fed to the anesthetic dispenser 23 via a line 63. Instead of the anesthetic tapping point 31, an anesthetic sensor (not shown) may also be arranged in the breathing tube 10. The anesthetic port 24 may also be led to the flexible inspiration tube 59 at a short distance after the anesthetic gas intermediate storage unit 12 (not shown). In addition, a breathing phase detector 18, which is connected to the control unit 19 by means of a data line 20, is connected to the flexible expiration tube 60 within the anesthetic gas module 35. The control unit 19 can thus synchronize, e.g., the motions of the gas lines 9a, 9b (not shown) for the two operating positions of the anesthetic gas intermediate storage unit 12 with the breathing cycle of the patient 5 and control them. Via a breathing gas outlet 7 at the respirator 1, the expiration gas flows to an adsorption filter 8, which is used to adsorb the residual quantity of anesthetic contained in the expiration gas in order to keep the ambient air free from anesthetic.

On the whole, inhalation sedation can be markedly improved with the anesthetic gas intermediate storage unit 12 according to the present invention. The use of two separate gas ducts 4, 6 for the inspiration gas and expiration gas together with port fittings that are free from dead space makes it possible to keep the overall dead space small. Because of the heatable adsorption material 2, which can be influenced electrically, the anesthetic concentration can be controlled easily and rapidly. Furthermore, sterilization of the adsorption material 2, which can be influenced electrically, by heating is possible, so that it is not necessary to remove the adsorption material for sterilization. The heating means for heating the adsorption material 2, which can be influenced electrically, can be arranged at the adsorption material at a low cost and with a low technical effort because the adsorption material 2, which can be influenced electrically, is stationary.

While specific embodiments of the invention have been shown and described in detail to illustrate the application of the principles of the invention, it will be understood that the invention may be embodied otherwise without departing from such principles.

APPENDIX

List of Reference Numbers

1 Respirator
2 Adsorption material, which can be influenced electrically
3 Openings (3a, 3b, 3c, 3d, 3e, 3f, 3g, 3h)
4 First gas duct for inspiration gas
5 Patient
6 Second gas duct for expiration gas
7 Breathing gas outlet
8 Adsorption filter
9 Gas lines (9a, 9b)
10 Breathing tube
11 Connector
12 Anesthetic gas intermediate storage unit 13 Empty bed
14 Empty bed
15 Adsorber bed
16 Adsorber bed
17 Drive means
18 Breathing phase detector
19 Control unit
20 Data line
21 Signal line
22 Respiration system
23 Anesthetic dispenser
24 Anesthetic port
25 Anesthetic measuring device
26 Signal line
27 Signal line
28 Regulator for the anesthetic concentration
29 Set point adjuster for the anesthetic concentration
30 HME filter
31 Anesthetic tapping point
32 Humidifier
33 Pivoting means
34 Diaphragm
35 Anesthetic gas module can be influenced electrically
36 Distributor fitting
37 Pipe fitting
38 Electromagnet
39 Insertion magnet
40 Cylindrical container
41 Partition
42 Carrier unit
43 Recesses
44 Electrodes
45 Housing
46 Flexible tube
47 Distributor plate
48 Hole
49 Sliding sealing ring
50 First end of pipe fitting
51 Second end of pipe fitting
52 Double port socket
53 Flexible tube
54 Measuring line
55 Part of adsorption material, which can be influenced electrically
56 Part of adsorption material, which
57 Port socket for expiration gas
58 Port socket for inspiration gas
59 Flexible inspiration tube
60 Flexible expiration tube
61 Pressurized gas source
62 Y-piece
63 Line

What is claimed is:

1. An anesthetic gas intermediate storage unit comprising:
a first gas duct for passing through inspiration gas;
a second gas duct for passing through expiration gas;
adsorption material with adsorption properties for an anesthetic carried by a gas which are influenced electrically, said adsorption material being arranged in at least one of said first gas duct for passing through breathing gas and said second gas duct for passing through breathing gas; and
a pivotable means at said adsorption material for diverting expiration gas and inspiration gas flowing in and out through one or more openings such that inspiration gas or expiration gas is alternatingly admitted to an identical area of said adsorption material, said pivotable means comprising a first gas line and a second line and means for alternating said first gas line and said second gas line between two operating positions relative to said adsorption material.

2. An anesthetic gas intermediate storage unit in accordance with claim 1, wherein said pivotable means carries out a rotary motion by said first gas line and said second gas line.

3. An anesthetic gas intermediate storage unit in accordance with claim 1, wherein said pivotable means comprises a drive means for moving said first gas duct and said second gas duct, said drive means comprising a stationary electromagnet and a movable insertion magnet or an electric motor.

4. An anesthetic gas intermediate storage unit in accordance with claim 1, wherein said adsorption material is stationary.

5. An anesthetic gas intermediate storage unit in accordance with claim 1, wherein said adsorption material includes an arrangement through which expiration gas and inspiration gas can flow.

6. An anesthetic gas intermediate storage unit in accordance with claim 1, wherein said first gas line and said second gas line comprise flexible tubes arranged concentrically one inside the other and fixed to a distributor plate.

7. An anesthetic gas intermediate storage unit in accordance with claim 1, wherein:
a pipe fitting with a movable diaphragm forms said first and said second gas line and said first gas line and said second gas line are movable upon movement of said diaphragm.

8. An anesthetic gas intermediate storage unit in accordance with claim 1, wherein said adsorption material comprises a cylindrical container and a first part separated gas-tightly from a second part of said adsorption material by a symmetrically arranged partition.

9. An anesthetic gas intermediate storage unit in accordance with claim 1, wherein said adsorption material comprises a first part and a second part arranged in a carrier unit in two duct-shaped recesses forming gas lines of said carrier unit.

10. An anesthetic gas intermediate storage unit in accordance with claim 9, wherein said carrier unit has a third and a fourth duct-shaped recess for flooding the anesthetic gas intermediate storage unit with fresh breathing gas and/or for an oxygen flush.

11. An anesthetic gas intermediate storage unit in accordance with claim 1, wherein said adsorption material comprises carbon fibers.

12. An anesthetic gas intermediate storage unit in accordance with claim 9, further comprising a heating means comprising one of heating electrodes and electric heating wires being integrated in the material, wherein said adsorption material is heated by electric current sent through said heating means.

13. An anesthetic gas intermediate storage unit in accordance with claim 12, wherein said first part and said second part of said adsorption material can be heated separately.

14. An anesthetic gas intermediate storage unit in accordance with claim 1, wherein said adsorption material comprises a removable container or carrier unit.

15. An anesthetic gas intermediate storage unit in accordance with claim 1, further comprising a housing.

16. An anesthetic gas intermediate storage unit in accordance with claim 1, wherein said pivotable means comprises at least one air valve moved by a drive means.

17. An anesthetic gas module comprising:
an anesthetic gas intermediate storage unit comprising adsorption material and a pivoting element, said pivoting element comprising a first gas line and a second line and means for alternating said first gas line and said second gas line between two operating positions relative to said adsorption material;

a set point adjuster;

a port fitting for connecting a respirator and a flexible expiration tube and a flexible inspiration tube for respirating a patient;

a drive means;

a control unit with a controller;

an anesthetic dispenser;

an anesthetic measuring device; and signal and data lines for connecting said anesthetic measuring device and/or said anesthetic dispenser and/or said drive means to said control unit.

18. An anesthetic gas module in accordance with claim 17, wherein said anesthetic gas intermediate storage unit comprises:

a first gas duct for passing through inspiration gas;

a second gas duct for passing through expiration gas, said adsorption material comprising adsorption properties for an anesthetic carried by a gas which are influenced electrically, said adsorption material being arranged in at least one of said first gas duct for passing through breathing gas and said second gas duct for passing through breathing gas.

19. A respiration system comprising:

a respirator;

a flexible expiration tube and a flexible inspiration tube for respirating a patient; and an anesthetic gas intermediate storage unit comprising:

a first gas duct for passing through inspiration gas;

a second gas duct for passing through expiration gas;

adsorption material with adsorption properties for an anesthetic carried by a gas which are influenced electrically, said adsorption material being arranged in at least one of said first gas duct for passing through breathing gas and said second gas duct for passing through breathing gas; and a pivotable means at said adsorption material for diverting expiration gas and inspiration gas flowing in and out through one or more openings such that inspiration gas or expiration gas is alternatingly admitted to an identical area of said adsorption material, said pivotable means comprising a first gas line and a second line and means for alternating said first gas line and said second gas line between two operating positions relative to said adsorption material.

20. A respiration system according to claim 19, wherein said anesthetic gas intermediate storage unit is part of an anesthetic gas module comprising, in combination with said anesthetic gas intermediate storage unit:

a set point adjuster;

a port fitting for connecting said respirator and said flexible expiration tube and said flexible inspiration tube for respirating the patient;

a drive means;

a control unit with a controller;

an anesthetic dispenser;

an anesthetic measuring device; and signal and data lines for connecting said anesthetic measuring device and/or said anesthetic dispenser and/or said drive means to said control unit.

21. A process for the intermediate storage of an anesthetic during the artificial respiration of a patient, the process comprising the steps of:

sending inspiration gas through a first gas duct and sending expiration gas through a second gas duct;

alternatingly admitting the expiration gas and inspiration gas to an adsorption material with adsorption properties for an anesthetic carried by a gas, which adsorption properties are influenced electrically, for adsorbing an anesthetic carried by the gas at least at one identical area for the intermediate storage of the anesthetic from the expiration gas to the inspiration gas, wherein expiration gas and inspiration gas flowing in and out are alternatingly diverted by a pivotable means, so that the inspiration gas and expiration gas are alternatingly admitted to the adsorption material, at least at one identical area, wherein said pivotable means is alternatingly moved with a first gas line and a second gas line between two operating positions relative to the adsorption material, in order to divert the expiration gas and the inspiration gas flowing in and out.

22. A process in accordance with claim 21, wherein said first gas line and said second gas line perform a rotary motion.

23. A process in accordance with claim 21, wherein said first gas line and said second gas line are moved between said two operating positions after one to three breathing cycles.

24. A process in accordance with claim 21, wherein the expiration gas and inspiration gas, which flow through said first gas duct and said second gas duct, are alternatingly admitted to a first part and a second part of said adsorption material.

25. A process in accordance with claim 21, wherein the inspiration gas and expiration gas are sent completely through said adsorption material.

26. A process in accordance with claim 21, wherein said adsorption material is heated.

27. A process in accordance with claim 26, wherein said adsorption material, to which inspiration gas is admitted, is heated during and/or shortly before an admission of inspiration gas in order to increase a concentration of the anesthetic in the inspiration gas.

28. A process in accordance with claim 26, wherein said adsorption material is heated during and/or shortly before a admission of expiration gas in order to lower a concentration of the anesthetic in the inspiration gas of a subsequent breathing cycle.

29. A process in accordance with claim 26, further comprising sterilizing said adsorption material by heating said adsorption material.

30. A process in accordance with claim 26, further comprising sending electric current through said adsorption material, to heat said adsorption material.

31. A process in accordance with claim 30, wherein the electric current is sent intermittently through different segments of said adsorption material.

32. A process in accordance with 30, wherein the electric current is sent with different voltages through said adsorption material.

33. A process in accordance with claim 21, further comprising providing a computer program with program code stored on a computer-readable data storage medium, for controlling said step of alternatingly admitting the expiration gas when the computer program is run on a computer or on a corresponding computing unit.

* * * * *